(12) United States Patent
Yun

(10) Patent No.: US 10,582,915 B2
(45) Date of Patent: Mar. 10, 2020

(54) FILM FOR ORAL HEMOSTASIS AND WOUND PROTECTION

(71) Applicants: TBM COMPANY, Gwangju (KR); GOOD THINKING CO., Gwangju (KR)

(72) Inventor: Seiyeong Yun, Gwangju (KR)

(73) Assignee: TBM Company, Gwangju (KR)

( * ) Notice: Subject to any disclaimer, the term of this patent is extended or adjusted under 35 U.S.C. 154(b) by 0 days.

(21) Appl. No.: 15/322,063

(22) PCT Filed: Oct. 28, 2016

(86) PCT No.: PCT/KR2016/012271
§ 371 (c)(1),
(2) Date: Dec. 23, 2016

(87) PCT Pub. No.: WO2017/090902
PCT Pub. Date: Jun. 1, 2017

(65) Prior Publication Data
US 2017/0296157 A1  Oct. 19, 2017

(51) Int. Cl.
| | |
|---|---|
| A61K 9/00 | (2006.01) |
| A61B 17/00 | (2006.01) |
| A61L 15/48 | (2006.01) |
| A61L 15/58 | (2006.01) |
| A61L 15/64 | (2006.01) |
| A61L 15/44 | (2006.01) |
| A61L 26/00 | (2006.01) |
| A61K 31/045 | (2006.01) |
| A61K 31/047 | (2006.01) |
| A61F 13/02 | (2006.01) |
| A61F 13/12 | (2006.01) |
| A61K 47/32 | (2006.01) |
| A61K 47/10 | (2017.01) |
| A61K 47/38 | (2006.01) |
| A61K 9/70 | (2006.01) |
| A61L 15/22 | (2006.01) |
| A61K 47/26 | (2006.01) |
| A61K 47/36 | (2006.01) |
| A61K 47/14 | (2017.01) |
| A61F 13/00 | (2006.01) |

(52) U.S. Cl.
CPC ...... *A61B 17/0057* (2013.01); *A61F 13/0256* (2013.01); *A61F 13/122* (2013.01); *A61K 9/006* (2013.01); *A61K 9/70* (2013.01); *A61K 31/045* (2013.01); *A61K 31/047* (2013.01); *A61K 47/10* (2013.01); *A61K 47/32* (2013.01); *A61K 47/38* (2013.01); *A61L 15/22* (2013.01); *A61L 15/44* (2013.01); *A61L 15/48* (2013.01); *A61L 15/58* (2013.01); *A61L 15/64* (2013.01); *A61L 26/009* (2013.01); *A61L 26/0066* (2013.01); *A61L 26/0071* (2013.01); *A61F 13/00* (2013.01); *A61K 47/14* (2013.01); *A61K 47/26* (2013.01); *A61K 47/36* (2013.01); *A61L 26/00* (2013.01); *A61L 2400/04* (2013.01)

(58) Field of Classification Search
CPC .................................................. A61B 17/0057
See application file for complete search history.

(56) References Cited

U.S. PATENT DOCUMENTS

| | | | | |
|---|---|---|---|---|
| 6,072,100 A | * | 6/2000 | Mooney | A61K 9/0014 424/448 |
| 6,375,963 B1 | * | 4/2002 | Repka | A61K 9/006 424/402 |
| 2006/0034905 A1 | * | 2/2006 | Singh | A61K 9/006 424/449 |

FOREIGN PATENT DOCUMENTS

KR  10-2005-0119914 A  12/2005
KR     10-0605290 B1    7/2006

OTHER PUBLICATIONS

Rabek et al.; Title: The effect of plasticizers on the erosion and mechanical properties of polymeric films; Journal of Biomateriaks applications, pp. 1-11; published 2013.*

* cited by examiner

Primary Examiner — Yanzhi Zhang

(57) ABSTRACT

The present disclosure relates to a film for oral hemostasis and wound protection and, more particularly, to a film for oral hemostasis and wound protection which, being attached to a wound area in an oral cavity, delays or prevents microbleeds and controls medicinal component release. The film provided by the present disclosure is capable of including a polyol, an alcohol and a biodegradable polymer in the state of partial swelling, thereby locally absorbing blood or pus or arresting hemorrhage. Moreover, due to its high elongation ratio, the film provided by the present disclosure is capable of maintaining its adhesive force even when having blood, saliva and pus absorbed inside an oral cavity and conveniently deforming according to the shape of a seriously corrugated local area, which causes only slight foreign body sensation even after a long period of time of attachment on to the local area. In addition, the film provided by the present disclosure includes a disintegrant which is dissolved and released by reacting with blood to form microchannels that act as paths for drug release and is capable of adjusting the amount and the size of the microchannels, thereby controlling the amount of drug release. The present disclosure doesn't require a patient to detach the film attached inside an oral cavity by hand because the adhesive layer and the backing layer dissolve entirely over time.

5 Claims, 1 Drawing Sheet

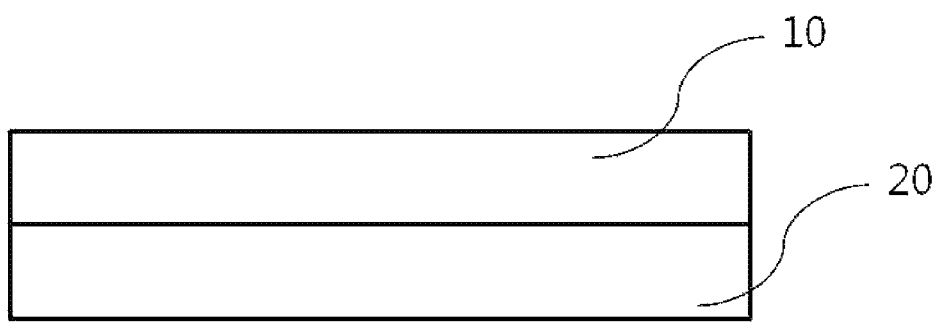

FILM FOR ORAL HEMOSTASIS AND WOUND PROTECTION

FIELD OF DISCLOSURE

The present disclosure relates to a film for oral hemostasis and wound protection and more particularly to a film for oral hemostasis and wound protection which, being attached to a wound area in an oral cavity, delays or prevents microbleeds and controls medicinal component release.

BACKGROUND

Drug delivery through oral mucosa is a significantly effective mode for drugs that easily lead metabolic reaction when orally administered, drugs with low bioavailability and drugs that cause gastrointestinal disorders. It is convenient to administer or remove such drugs through or from oral mucosa. In addition, oral mucosa are less sensitive to stimuli or damage than other kinds of mucosa are. For such reasons, oral mucosa have attracted attention as a new path for drug administration. Therefore, the mode can be used not only for simply treating diseases in an oral cavity but for administering those drugs that are capable of being systemically delivered only in a small amount.

Although such drugs that are administrable through oral mucosa are, for the most part, liquid-, troche- or ointment-based, these are applied in a bolus which is not consistent and, after being applied, easily dissolves by means of saliva, which restrains the drugs from taking their medicinal efficacy in a constant way.

Korean Patent No. 10-065290 B1 discloses a technology which prevents a liquid or gel drug from being easily lost by forming a protective film on the surface of the drug so as to keep the drug away from moisture penetration such as saliva. However, even when such protective films are formed on a gel surface, it is difficult to use the films for a long time and, furthermore, such films rather inhibit drug release depending on polymer species or layer thickness.

Films, e.g. RAPIDFILM and tesa Labtec GmbH that stick to oral mucosa have recently been developed in order to solve the problems inherent in such ointment- or gel-based drugs. Although such sticky films are capable of being administered in a constant bolus and expressing their medicinal efficacy in a consistent way, it has been raised as an issue about such sticky films that all their major components are wholly released either locally in an oral cavity or momentarily in a digestive organ because the film is entirely dissolved in a short period of time that amounts to three minutes or so.

Meanwhile, Korean Patent Application Publication No. 10-2005-0119914 discloses a sheet that is stuck to teeth and gingiva for a long period of time. However, the sheet, comprising four layers, should keep a relatively large thickness, which causes foreign body sensation when being stuck to oral mucosa to lower patient compliance and swelling with saliva for the sheet to be easily detached from the oral mucosa. In addition, because the sheet includes a water insoluble sticky layer, a patient should detach with their hand the sheet that is attached in their oral cavity, which raises issues of hygiene and inconvenience of use. Although a few drugs that are rapidly dissolved and released in the Korean and overseas markets, there have been introduced no mucosa-attachable drugs which are attached inside an oral cavity to control-release medicinal substances. As actual exemplification, Breath Strips manufactured by Listerine of the US, and a few other products similar thereto, assume the shape of a film, which is dissolved within about three minutes in an oral cavity.

The above information disclosed in this Background section is only for enhancement of understanding of the background of the disclosure and it may therefore contain information that does not form the prior art that is already known to a person of ordinary skill in the art. The present disclosure relates to a film for oral hemostasis and wound protection and more particularly to a film for oral hemostasis and wound protection which, being attached to a wound area in an oral cavity, delays or prevents microbleeds and controls medicinal component release.

SUMMARY OF THE DISCLOSURE

Technical Problem

The present disclosure provides a film for oral hemostasis and wound protection which is, attached onto oral mucosa, capable of absorbing blood or emulsifying pus.

The present disclosure provides the film for oral hemostasis and wound protection which is attached inside an oral cavity for a period of time of ten minutes or more and controls medicinal substance release.

The present disclosure provides the film for oral hemostasis and wound protection which causes no foreign body sensation of a patient and is not easily removed inside an oral cavity.

The present disclosure provides the film for oral hemostasis and wound protection which doesn't require a patient to detach a sheet attached inside their oral cavity by hand.

Technical Solution

An aspect of the present disclosure includes an adhesive layer which includes a hydrophilic polymer, a disintegrant and any one or more among a surfactant, oil and a plasticizer and is stuck onto a wound area to delay or prevent microbleeds; and a backing layer which includes a water insoluble polymer and is placed on the adhesive layer to protect the adhesive layer, inside an oral cavity, from the tongue, saliva or food, wherein the disintegrant is dissolved and released by reacting with blood to form microchannels inside the adhesive layer.

Advantageous Effects

The film provided by the present disclosure is capable of including a polyol, an alcohol and a biodegradable polymer in the state of partial swelling, thereby locally absorbing blood or pus or arresting hemorrhage. Moreover, due to its high elongation ratio, the film provided by the present disclosure is capable of maintaining its adhesive force even when having blood, saliva and pus absorbed inside an oral cavity and conveniently deforming according to the shape of a seriously corrugated local area, which causes only slight foreign body sensation even after a long period of time of attachment on the local area. In addition, the film provided by the present disclosure includes a disintegrant which is dissolved and released by reacting with blood to form microchannels that act as paths for drug release and is capable of adjusting the amount and the size of the microchannels, thereby controlling amount of drug release.

The present disclosure doesn't require a patient to detach the film attached inside an oral cavity by hand because the adhesive layer and the backing layer entirely dissolve over time

BRIEF DESCRIPTION OF DRAWINGS

The above and other features and advantages of the present disclosure will be more clearly understood from the following detailed description taken in conjunction with the accompanying drawing, in which:

FIG. 1 is a schematic view of the film for oral hemostasis and wound protection according to the present disclosure.

DETAILED DESCRIPTION OF THE EMBODIMENTS

The present disclosure will be described more fully hereinafter with reference to the accompanying embodiments and examples. However, the present disclosure may be embodied in many different forms, and should not be construed as being limited to the embodiments set forth herein.

FIG. 1 is a schematic view of the film for oral hemostasis and wound protection according to the present disclosure. With reference to FIG. 1, the film includes an adhesive layer 10 and a backing layer 20.

The adhesive layer 10 comes, on one of its surfaces, in contact with and is attached to hard or soft tissue inside an oral cavity while the backing layer 20 is formed on the other surface of the adhesive layer 10 and prevents the adhesive layer from being dissolved by means of the tongue or saliva.

The adhesive layer 10 includes any one or more among a surfactant, oil and a plasticizer along with a hydrophilic polymer and a disintegrant while the adhesive is capable of further including an additional drug.

The hydrophilic polymer functions as the base material of the adhesive layer and a polymer which generates adhesive force when being hydrated is selected as the hydrophilic polymer. For example, one or more species can be selected as the hydrophilic polymer from a group consisting of: carboxymethyl cellulose, carboxypropyl cellulose or ones made of their salts, hydroxyethyl celluose, hydroxypropyl cellulose, hydroxypropylmethyl cellulose and hydroxypropylethyl cellulose as celluose based polymers; gelangum, xanthan gum, guar gum, carrageenan gum, karayan gum, arabic gum and alginate gum or their salt derivatives as gum based polymers; and povidone, polyvinyl alcohol, poloxamer, polyvinyl pyrrolidone, polyvinyl pyrrolidone-vinyl acetate copolymers, polyacryllic acid, carbopol, polyquatemium-11, 39, PVM/MA copolymer: Gantgrez AN 119, 139, S-97 and polyox as gelatins and synthetic polymers.

The adhesive layer includes any one or more among a surfactant, oil and a plasticizer, wherein the surfactant is capable of maintaining the disintegrant or a lipophilic softener, which is described below, in their stable state in a hydrophilic solvent.

Various species of the surfactant can be used including negative ionic, positive ionic or amphoteric ionic ones which are pharmaceutically permissible. For example, at least one species can be selected as the surfactant from a group consisting of polyoxyethylene glycolized natural or hydrogenated castor oil, ester of mono- or tri-lauryl, palmityl, stearyl or oleyl, polyoxyethylene stearic acid ester, polyoxyethylene-polyoxypropylene copolymers, polyoxyethylene-polyoxypropylene block copolymers, sodium sulfosuccinate or sodium lauryl sulfate, phospholipids, propylene glycol dicaprylate, propylene glycol dilaurate, propylene glycol isostearate, propylene glycol laurate, propylene glycol recinoleate or propylene glycol caprylic-capric acid diester, reaction products of transesterification between a natural vegetable oil triglyceride and a polyalkylene polyol, capryl/capric acid mono- or diglycerides, sorbitan fatty acid esters, sorbitan monolauryl, sorbitan monopalmityl or sorbitan monostearyl, colesterol, phytosterol and sitosterol.

Silicone oil, liquid paraffin, rosin wax solutions, soybean oil, olive oil, sesami oil, castor oil, fat soluble vitamins, fat soluble vitamin acetates and others can be used as the oil while the oil functions also as the plasticizer.

The plasticizer, which is used so as to provide the film with flexibility and elasticity, can be selected from a group consisting of acetyl triethyl citrate, citrate ester, triacetin and triethyl citrate.

The disintegrant is dissolved and released when it reacts with blood, thereby forming microchannels inside the adhesive layer while the drug is released via the microchannels, wherein it is possible to control the size and the distribution of the microchannels by adjusting content of the disintegrant, thereby adjusting the amount of release of the drug.

Any one or more can be selected as the disintegrant from glycol, glycerin, sorbitol, polyol such as PEG, xylitol lactose, magnesium stearate, crystalline cellulose and crospovidone.

The drug includes all agents appropriate to absorption from oral mucosa and known therapies for oral cavities, periodontal wound dressings among others can also fall into the drug. For example, the drugs which can be used for the film according to the present disclosure include agents for treating oral diseases such as antiinflammatory agents and disinfectants, antihistamine medications, tissue restoring agents, hemostatic agents, hormone medications, hypertension medications, antibiotics, bronchodilators and others.

The antiinflammatory agents include tranexamic acid, lysozyme chloride, sodium azulen sulfonate, dipotassium glycyrrhizate, glycyrrhizic acid, ammonium glycyrrhizate, glycyrrhetinic acid, bromelain, serrapeptase, pranoprofen, ibuprofen piconol, presteron, lithospermum root extract, epidihydrocholesterin, bufexamac, myrrh tincture, bupleurum falcatum L., wolfporia cocos, phellodendron bark, hydrocortisone acetate, prednisolone acetate, prednisolone, hydrocortisone, triamcinolone acetonide and others.

The disinfectants include potassium iodide, liquefied phenol, phenol, cetylpyridinium chloride, chlorhexidine gluconate, chlorhexidine hydrochloride, dequalinium chloride, creosote, thymol, triclocarban, benzalkonium chloride, benzethonium chloride, acrinol, oxydol, ethanol, isopropanol, mercurochrome, cresol, isopropyl methylphenol, phenyl salicylate, sulfadiazine, homosulfamin, cassia bark oil and others.

The antihistamine medications include chlorpheniramine maleate, diphenhydramine salicylate, diphenylpyraline hydrochloride, mequitazine, triprolidine hydrochloride, carbinoxamine maleate, diphenhydramine hydrochloride, diphenhydramine tannate, dimenhydrinate, promethazine hydrochloride, promethazine teoclate, meclizine hydrochloride, isopentyl hydrochloride and others.

The tissue restoring agents include sodium copper chlorophyllin, allantoin, aldioxa, methylmethioninesulfonium chloride, sucralfate, asiaticoside, cetraxate hydrochloride, sofalcone, gefarnate, trimeptin maleate, teprenone, heparin-like substances and others.

Topical medications include dibucaine hydrochloride, dibucaine, lidocaine hydrochloride, lidocaine, ethyl aminobenzoate, oxethazaine, and others.

The rest of the components includes local protectants such as glycerin and concentrated glycerin, local stimulants such as I-menthol, peppermint oil and dl-menthol, hemostatics such as carbazochrome, vitamin preparations such as ascorbic acid, calcium ascorbate, tocopherol acetate, tocopherol calcium succinate, pantothenol and pyridoxine hydrochloride, blood circulation improving drugs such as benzyl nicotinate, blood circulation improving drugs such as sodium polyethylene sulfonate and antibiotic substances such as minocycline hydrochloride.

The adhesive layer can include, when the hydrophilic polymer is 100 parts by weight, 0.1 to 60 parts by weight of the surfactant, the oil or the plasticizer and 0.1 to 30 parts by weight of the disintegrant.

The adhesive layer can include, when the hydrophilic polymer is 100 parts by weight, 0.1 to 60, desirably 1 to 40 or more desirably 1 to 30 parts by weight of the surfactants or the oil.

The adhesive layer can include, when the hydrophilic polymer is 100 parts by weight, 0.1 to 60, desirably 1 to 40, more desirably 1 to 20 or still more desirably 1 to 15 parts by weight of the plasticizer.

When the hydrophilic polymer is 100 parts by weight, 0.1 to 30, desirably 1 to 25 or more desirably 1 to 20 parts by weight of the disintegrant can be used.

The adhesive layer can include, when the hydrophilic polymer is 100 parts by weight, 0.01 to 20 parts by weight of the drug.

The adhesive layer can contain 0.1 to 30 wt % of water, thereby being partially swollen, and be stuck onto oral mucosa. When the adhesive layer contains water within the range described above, the adhesive layer is kept swollen for a long period of time, thereby being capable of absorbing blood or pus more rapidly. That the adhesive layer is partially swollen means that it is not fully swollen.

The adhesive layer can further include 0.1 to 30 parts by weight of the lipophilic softener when the hydrophilic polymer is 100 parts by weight.

Although, the hydrophilic polymer and the drug included in the adhesive layer are gradually consumed because they are dissolved by means of saliva, the lipophilic softener raises its relative content in the adhesive layer over time because the lipophilic softener is not dissolved by saliva. The lipophilic softener, the relative content of which has been increased, slowly infiltrates into the adjacent backing layer and softens the backing layer 20 and, as a result, the backing layer dissolves by means of saliva.

In other words, the softener of the present disclosure transfers over time from the adhesive layer 10 to the backing layer 20 making the backing layer, which is water insoluble, softened and dissolving. Consequently, the adhesive layer is prevented from being rapidly decomposed and the drug is sustainedly released because the backing layer slowly dissolves, which explains the drug delivery system of the present disclosure.

It is possible to control drug release time and drug release content of a drug carrier, or the film, depending on the content of the softener and the thickness of the backing layer.

The softener can be any one selected from triethyl citrate, dibutyl sebacate, acetyl triethyl citrate and triacetin.

The adhesive layer can be formed by dissolving the components in a solvent and then drying them. The solvent can be prepared by using water, methanol, ethanol, acetone, isopropanol, ethyl acetate and others and it may be required to use water for the solvent.

The adhesive layer can have a thickness of 50 to 1,500 μm, desirably 100 to 1,200 μm or most desirably 600 to 1,200 μm.

The backing layer 20 can be manufactured by blending a water insoluble polymer with a solvent. The backing layer is placed on the adhesive layer and plays a role in protecting the adhesive layer from the tongue and food inside an oral cavity. The backing layer 20 can be softened and lost by means of the softener of the adhesive layer as described earlier.

The backing layer 20 can have a thickness of 5 to 300 μm, desirably 10 to 150 μm or most desirably 10 to 80 μm.

The water insoluble polymer can be a separate one among or a mixture of polyvinyl acetate, ethyl cellulose, polymethyl methacrylate, methacrylic acid copolymers such as methacryloylethyl betaine/methacrylate copolymers (yukaformer), methacrylic copolymers and aminoalkyl methacrylate copolymers (Eudragit E, RL), cellulose acetate phthalate, shellac, polyethylene, PVC, polyurethane and polyethylene.

The backing layer can be manufactured by additionally dissolving the surfactant and the plasticizer or the oil and the softener in the solvent.

The present disclosure is now described below more specifically with the following embodiments and comparative examples for the purpose of easy understanding, but not limited thereto.

Embodiments 1 Through 7, Comparative Examples 1 Through 4

An adhesive solution and a backing solution were prepared by using the components listed in Tables 1 and 2. First, the adhesive solution was applied on a thin detached layer and then dried to manufacture an adhesive layer film. Second, the backing solution was applied on the adhesive layer film and then dried. A double layer film manufactured according to the method was cut to a predetermined size.

TABLE 1

| Ingredients | components | Example | | | | | | | Comparative Example | |
|---|---|---|---|---|---|---|---|---|---|---|
| | | 1 | 2 | 3 | 4 | 5 | 6 | 7 | 1 | 4 |
| surfactant | Sorbitan monooleate | 5 | 5 | 5 | 5 | 5 | 3 | 5 | | |
| | Sorbitan Fatty Acid Ester | 5 | 4 | 5 | 4 | 4 | 4 | 4 | | |
| | polyoxyethylene-polyoxypropylene block copolymers | | | 1 | | | | | | |
| | sodium lauryl sulfate | | | | | 1 | 1 | 1 | 1 | |
| Oil/plasticizer | Silicone oil | 1 | | | | 1 | 1 | 1 | | |
| | liquid paraffin | 4 | 5 | | | | | | | |
| | castor oil | | | 5 | 5 | 4 | 4 | 4 | | |

TABLE 1-continued

| Ingredients | components | Example 1 | Example 2 | Example 3 | Example 4 | Example 5 | Example 6 | Example 7 | Comparative Example 1 | Comparative Example 4 |
|---|---|---|---|---|---|---|---|---|---|---|
| softener | triethyl citrate | 5 | | 5 | | | 5 | | 5 | 5 |
| | dibutyl sebacate | | 5 | | | | | 5 | | |
| | acetyl triethyl citrate | | | | 5 | 1 | 1 | 1 | | |
| polymer | hydroxyethyl cellulose | 5 | | 5 | 5 | 34 | 26 | 15 | | |
| | Povidone | 52 | 45 | | | 25 | | 24 | | |
| | polyvinyl alcohol | | 5 | 50 | 60 | | 20 | 15 | | |
| | xanthan gum | | 2 | | | 5 | | | | |
| | carbopol 934P | | | | | | | | 4 | 4 |
| | hydroxypropyl cellulose | | | | | | | | 24 | 24 |
| disintegrant | crospovidone | 3 | 5 | 5 | | | 5 | 5 | | |
| | Propylene Glycol | | | 2 | 2 | 2 | 1 | | | |
| | PEG-400 | | 1 | | 2 | 5 | | 2 | | |
| | glycerin | | | | | 5 | | | | |
| | sorbitol | | | | | 2 | | | | |
| drug | Vitamin E | 1 | | | | | | | | |
| | CPC(Cetylpyridinium chloride) | | | 0.1 | | | | | | |
| | Dexamethasone | | 0.1 | | | | | | 0.1 | |
| | dibucaine hydrochloride | | | | | | | | | |
| Additive | Pigment Blue #1(1% Sol'n) | 1 | 1 | 1 | | | | | 1 | |
| | perfume | 1 | 1 | 1 | | | | | | |
| | Ph adjuster | 0.1 | | | | | | | | |
| solvent | water | 16.9 | 19.9 | 15.9 | 5.9 | 9.9 | 30 | 10 | | |
| | ethanol | | | | 1 | 1 | 1 | | TO 200 | TO 200 |
| | acetone | | | | 2 | | | | | |
| Total | | 100 | 100 | 100 | 99.9 | 99.9 | 96 | 86 | | |

Comparative Example 2 was employed with a Reso-Pac®, Comparative Example 3 was employed with a gauze for dental treatment.

TABLE 2

| Ingredients | components | Example 1 | Example 2 | Example 3 | Example 4 | Example 5 | Example 6 | Example 7 | Comparative Example 1 | Comparative Example 4 |
|---|---|---|---|---|---|---|---|---|---|---|
| surfactant | Sorbitan monooleate | 2 | | | | | 2 | | | |
| | Sorbitan Fatty Acid Ester | | 4 | 2 | 4 | 4 | 4 | | | |
| | polyoxyethylene-polyoxypropylene block copolymers | | 1 | | 1 | 1 | 1 | | | |
| | sodium lauryl sulfate | | | 1 | | | | | | |
| Oil/plasticizer | glycerin | 1 | 1 | | 1 | 1 | 1 | | | |
| | liquid paraffin | 1 | 2 | | 2 | 2 | 2 | | | |
| softener | triethyl citrate | 5 | | 5 | | | | | 18 | 18 |
| | dibutyl sebacate | | 5 | | 5 | | 5 | | | |
| | acetyl triethyl citrate | | | | | | | | | |
| polymer | Polyvinyl acetate | | | 5 | | | | | | |
| | ethyl cellulose | 50 | 65 | | 65 | 65 | 65 | | 18 | 18 |
| | Methyl Methacrylate Copolymer | | 5 | 50 | 5 | 5 | 5 | | | |
| | Polyethylene | | | | | | | 100 | | |
| | Methacrylic Acid-Methyl Methacrylate Copolymer | | | | | | | | 18 | 18 |
| solvent | ethanol | TO 100 | TO 100 | TO 100 | TO 100 | TO 100 | TO 100 | TO 100 | TO 100 | TO 100 |
| | acetone | | | 2 | 2 | | | | | |
| Total | | | | 102 | 102 | | | | | |

Experiment 1: Dissolution Rate Test

The films for oral hemostasis and wound protection (hereinafter referred to as the 'hemostatic film') prepared in Embodiments 1 through 3 and Comparative Example 1 were employed as the specimens for the dissolution rate test. The test was performed according to the second dissolution rate test method (Paddle method) stipulated in the Korean Pharmacopoeia. More specifically, the dissolution was performed in an eluate of 900 ml, which was maintained at pH 6.8 and at 37±0.5° C., where a paddle rotated at 50 rpm. The eluted was sampled after 5 minutes through 1 hour at an interval of 10 minutes. Substances dissolved were identified with Blue #1, the pigment, and evaluated with naked eyes according to a 5-step scale of the extent of the release.

TABLE 3

| Test time | | Dissolution rate | | | |
| --- | --- | --- | --- | --- | --- |
| | | Example | | | Comparative Example |
| No | Time | 1 | 2 | 3 | 1 |
| 1 | 1 minute | 1 | 1 | 2 | 1 |
| 2 | 5 minute | 2 | 3 | 3 | 1 |
| 3 | 10 minute | 3 | 4 | 4 | 2 |
| 4 | 30 minute | 4 | 4 | 4 | 3 |

4 point scale; 1: Transparent, 2: Pale Blue, 3: Blue, 4: Dark Blue

Table 3 shows that Embodiments 1 through 3 released the pigment in periods shorter than that of Comparative Example 1. In addition, Comparative Examples 2 and 3, which contained more of the disintegrant than Embodiment 1, released the pigment faster. In other words, Table 1 reveals that specimens with more of the disintegrant released faster. Therefore, controlling the content of the integrant can control the rate the substances are released at.

Experiment 2: Evaluation of Degree of Wound Healing

Degree of wound healing was evaluated with the hemostatic films prepared in Embodiments 4 through 6 and Comparative Examples 2 through 4. 72 male Sprague Dawley rats, 16 to 18 weeks old, were divided into 3 groups and stored in standard raising cases. The rats were anaesthetized with 5% isoflurane, ketamine hydrochloride and xylaizne and topically with lidocaine. Trephine burs were used to cut surgical defects on the rats, where a calvarial defect procedure was employed on the experimental group and the controlled group. The defects were sutured and, after 4 and 8 weeks, respectively, the degrees of wound healing were compared as listed in Table 4.

TABLE 4

| Test time | | Degree of wound healing | | | |
| --- | --- | --- | --- | --- | --- |
| | | Example | | | Comparative Example |
| No | Time | 3 | 4 | 5 | 2 | 4 |
| 1 | 4 week | 3 | 2 | 3 | 1 | 1 |
| 2 | 8 week | 4 | 3 | 3 | 2 | 2 |

4 point scale; 4: Excellent, 3: Very Good, 2: Good, 1: Average

As listed in Table 4, Embodiment 3 had an effect higher, due to CPC, the disinfecting component, than that of Embodiment 4. Although Embodiments 4 and 5 showed effects similar to each other, Embodiment 5 was slightly more effective because, presumably, Embodiment 5 had a higher content of the disintegrant and water. This component can preferentially protect dried skin.

Reso-Pac® as Comparative Example 2 is an ointment preparation. The preparation vanishes over time when it is applied on a wound area, which explains why it is less effective in protecting such wounds. No surfactant was employed in Comparative Example 4. Therefore, it is thought that it was difficult to protect, with tight feel, a corrugated wound area on which oil-based components remained and that an overdose of alcohol also generated a reverse synergetic consequence.

Experiment 3: Evaluation of Degree of Hemostasis Prevention

The hemostatic films prepared in Embodiments 4 through 6 and Comparative Examples 1 through 3 were employed in evaluating degree of hemostasis prevention, as listed in Table 5. ASTM D570, Standard Test Method for Water Absorption of Plastics, was applied as the evaluation method. The hemostatic films were cut to 10 mm by 10 mm and contained beneath a mesh. 0.9% normal saline water solution was filled in a sprayer and sprayed on the hemostatic films beneath the mesh. The films were placed on nonwoven fabric to absorb remaining water. Then, the films were compressed and pressed under a 10 g of weight to remove water formed on the surface. Weight of the remaining specimens save for the mesh was calculated and absorption power was measured according to the formula described below. Whether absorption of water could be faster depending on the water content inside the adhesive layer was assessed.

Absorption ratio, $A=(Wa-Wo)/Wo*100$ where Wo and Wa is weight of the film before the absorption and after the spraying, respectively.

TABLE 5

| Absorption ratios(%) | | | | | |
| --- | --- | --- | --- | --- | --- |
| Example | | | Comparative Example | | |
| 4 | 5 | 6 | 1 | 2 | 3 |
| 173 | 165 | 145 | 117 | 101 | 125 |

(4 point scale; 4: Excellent, 3: Very Good, 2: Good, 1: Average)

Embodiments 4 through 6 showed absorption ratios higher than those of Comparative Examples 1 through 3. The ratio was lowest in Reso-Pac® of Comparative Example 2. The gauze of Comparative Example 3 absorbed a certain amount of water when sprayed by the sprayer and discharged the absorbed water when pressed under the weight of 10 g. Therefore, it is thought that such a phenomenon corresponds to that the gauze was easily detached when it physically came in contact with the tongue and others inside an oral cavity. Lower water content was advantageous in preventing the hemostatic components. Degree of swelling varied depending on the water content inside the adhesive layer, where it was shown that the faster the absorption of water or pus was performed, the lower was water content.

Experiment 4: Usability Evaluation

Usability of the hemostatic films prepared in Embodiments 5 and 6 and Comparative Examples 2 through 4 was evaluated and listed in Table 6. Degree of satisfaction with the specimens attached inside an oral cavity was determined as the usability. Thirty subjects were selected for the evaluation.

TABLE 6

| Degree of satisfaction | | | | |
| --- | --- | --- | --- | --- |
| Example | | Comparative Example | | |
| 5 | 6 | 2 | 3 | 4 |
| 3.5 | 3.7 | 2.5 | 1.5 | 2.4 |

(4 point scale; 1: poor, 2: a slightly poor, 3: convenience 4: very convenience)

Embodiments 5 and 6 gained higher scores than Comparative Examples 2 through 4 did. It is thought that Embodiment 6 gained a still higher score because a synergetic effect generated by the surfactant, the plasticizer and the softener it contained. However, only the surfactant and the plasticizer/oil without the softener can show efficacy to a certain extent. It is thought that the components referred to above functioned when they provided conditions where the functional groups of the polymers of the preparation were combined well with the surface of oral mucosa at the microscopic level when the branches of the polymers of the preparation were softened at the molecular level. In contrast, Comparative Example 2 provided considerable, ointment induced foreign body sensation. Although the gauze of Comparative Example 3 was capable of absorbing fluids due to its own nature, it showed poor performance of hemostasis, which brought out the lowest satisfaction. Comparative Example 4, in which only the softener was employed, didn't show high usability.

Those skilled in the art will appreciate that the conceptions and specific embodiments disclosed in the foregoing description may be readily utilized as a basis for modifying or designing other embodiments for carrying out the same purposes of the present disclosure. Those skilled in the art will also appreciate that such equivalent embodiments do not depart from the spirit and scope of the disclosure as set forth in the appended Claims.

What is claimed is:

1. A film for oral hemostasis and wound protection comprising:
   an adhesive layer comprised of water at between 5.9 and 15.9% of the total weight of the film, a hydrophilic polymer, a disintegrant and at least one material selected from the group consisting of a surfactant, oil, and a plasticizer, configured to attach to a wound area to delay or prevent microbleeds; and
   a backing layer comprised of a water insoluble polymer configured to affix to the adhesive layer to protect the adhesive layer, from the tongue, saliva, or food,
   wherein the disintegrant is dissolved and released by reacting with blood to form microchannels inside the adhesive layer,
   wherein the disintegrant is at least one material selected from the group consisting of polyethylene glycol, glycerin, and sorbitol;
   wherein the film is manufactured by a process of:
   dissolving the components of the adhesive layer in water to form an adhesive solution;
   depositing the adhesive solution in a layer and drying it;
   dissolving the components of the backing layer to form a backing solution, applying the backing solution to the adhesive layer, and drying;
   to achieve a the water content of the adhesive layer is between 5.9 and 15.9% by weight.

2. The film for oral hemostasis and wound protection of claim 1, wherein the adhesive layer includes, 3 to 5 parts by weight of the surfactant, the oil, or the plasticizer and 1 to 5 parts by weight of the disintegrant, by the total weight of the film.

3. The film for oral hemostasis and wound protection of claim 1,
   wherein the adhesive layer includes 0.1 to 30 parts by weight of a lipophilic softener per 100 parts by weight of the hydrophilic polymer, wherein the softener infiltrates into the backing layer to soften the backing layer such that the softened backing layer slowly dissolves by means of saliva as the adhesive layer is gradually consumed in the oral cavity, wherein the softener is a material selected from the group consisting of triethyl citrate, dibutyl sebacate, and acetyl triethyl citrate.

4. The film for oral hemostasis and wound protection of claim 1, wherein the film further includes a drug, wherein the drug is an anti-inflammatory agent, an agent for treating oral diseases, an antihistamine medication, a hormone medication, a hypertension medication, an antibiotic or a bronchodilator, wherein the amount of drug included is 0.01 to 20 parts per 100 weight of the hydrophilic polymer.

5. The film for oral hemostasis and wound protection of claim 1, wherein
   the adhesive layer comprises PEG 400.

* * * * *